(12) United States Patent
Breslich

(10) Patent No.: US 10,610,212 B2
(45) Date of Patent: Apr. 7, 2020

(54) LOCKING SUTURE CONSTRUCT

(71) Applicant: Conmed Corporation, Utica, NY (US)

(72) Inventor: Grady Breslich, Bradenton, FL (US)

(73) Assignee: CONMED CORPORATION, Utica, NY (US)

( * ) Notice: Subject to any disclaimer, the term of this patent is extended or adjusted under 35 U.S.C. 154(b) by 193 days.

(21) Appl. No.: 15/630,215

(22) Filed: Jun. 22, 2017

(65) Prior Publication Data

US 2018/0353166 A1 Dec. 13, 2018

Related U.S. Application Data

(60) Provisional application No. 62/518,749, filed on Jun. 13, 2017.

(51) Int. Cl.
*A61B 17/04* (2006.01)
*A61B 17/06* (2006.01)

(52) U.S. Cl.
CPC ...... *A61B 17/0401* (2013.01); *A61B 17/0487* (2013.01); *A61B 17/06166* (2013.01); *A61B 17/0485* (2013.01); *A61B 2017/0404* (2013.01); *A61B 2017/0406* (2013.01); *A61B 2017/0409* (2013.01); *A61B 2017/0414* (2013.01); *A61B 2017/0445* (2013.01); *A61B 2017/0458* (2013.01); *A61B 2017/0475* (2013.01); *A61B 2017/0477* (2013.01); *A61B 2017/06185* (2013.01)

(58) Field of Classification Search
CPC .......... A61B 17/0487; A61B 17/06166; A61B 17/0485; A61B 2017/0404; A61B 2017/0406; A61B 2017/0409
See application file for complete search history.

(56) References Cited

U.S. PATENT DOCUMENTS

| 5,540,703 | A  | 7/1996 | Barker, Jr. et al. |
| 8,795,334 | B2 | 8/2014 | Astorino et al. |
| 9,060,764 | B2 | 6/2015 | Sengun |
| 9,078,651 | B2 | 7/2015 | Astorino et al. |

(Continued)

OTHER PUBLICATIONS

Ronald Glousman, M.D. and Nicholas Sgaglione, M.D., Labral Repair, JuggerKnot Soft Anchor brochure, 2010, 2011, 12 pages.

(Continued)

*Primary Examiner* — Tuan V Nguyen

(74) *Attorney, Agent, or Firm* — Frederick JM Price; Bond, Schoeneck & King, PLLC

(57) ABSTRACT

A locking suture construct having suture material with a first end and a second end, each attached to a first body in a slidable manner, a constricting member formed in the second end of the suture material, and a bight in the suture material between the first end and the second end. The bight can be pulled through the constricting member around a second body to create a locking loop. The first end and the second end are passed through the locking loop. Pulling the first end increases a perimeter of the locking loop and moves the constricting member toward the second body. When the constricting member reaches the second body, pulling the first end reduces the perimeter of the locking loop and moves/rotates the constricting member around the second body toward the first body to hold the first body in relative position to the second body.

7 Claims, 27 Drawing Sheets

(56) References Cited

U.S. PATENT DOCUMENTS

| | | |
|---|---|---|
| 9,314,241 B2 | 4/2016 | Stone et al. |
| 9,370,352 B2 | 6/2016 | Astorino et al. |
| 9,402,620 B2 | 8/2016 | Pilgeram |
| 9,504,462 B2 | 11/2016 | Dooney, Jr. et al. |
| 2008/0082127 A1* | 4/2008 | Stone ................. A61B 17/0401 606/232 |
| 2009/0076547 A1 | 3/2009 | Sugimoto et al. |
| 2013/0096612 A1 | 4/2013 | Zajac et al. |
| 2017/0049432 A1* | 2/2017 | Dooney, Jr. ........ A61B 17/0401 |

OTHER PUBLICATIONS

European Patent Office Report, EPO Form 2001, Application No. 12 748 076.2, pp. 1-4, dated Mar. 2, 2017.

* cited by examiner

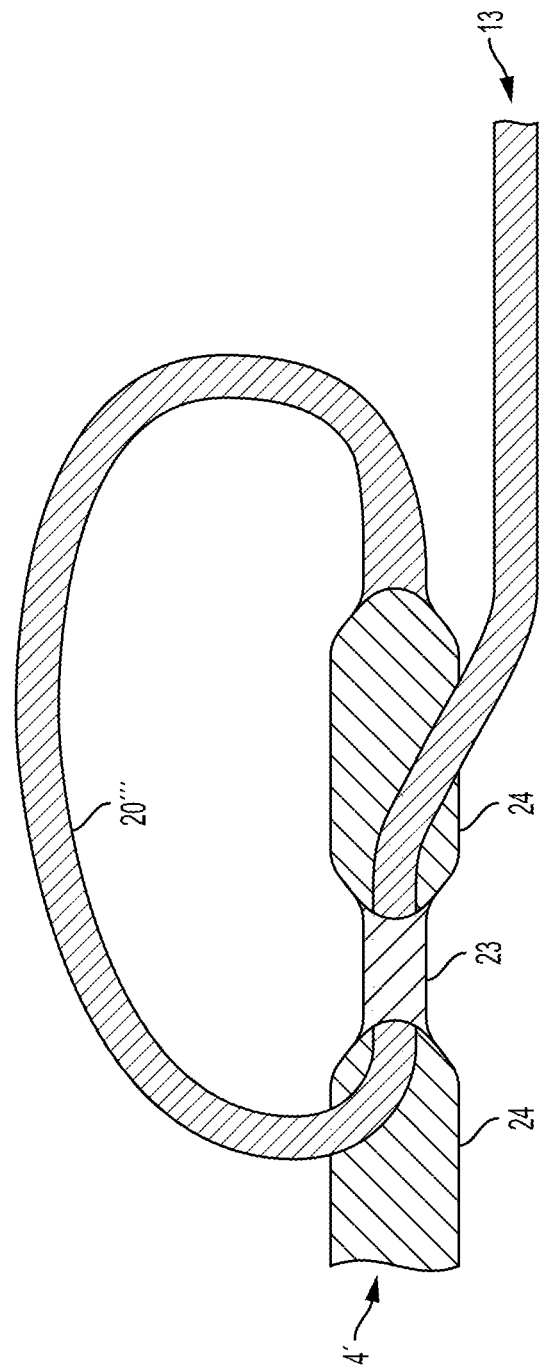

LOCKING SUTURE CONSTRUCT

CROSS-REFERENCE TO RELATED APPLICATIONS

The present application claims priority to and the benefit of U.S. Provisional Patent Application No. 62/518,749, filed on Jun. 13, 2017, the entire contents of which are hereby incorporated by reference.

BACKGROUND OF THE INVENTION

Field of the Invention

The present invention is related to an adjustable locking construct for fixation of two bodies at a surgical/repair site and, more particularly, to an adjustable suture loop construct for fixing the relative position of two bodies at a surgical/repair site.

Description of the Related Art

Sutures with traditional knots or knotless constructs are often employed for reduction and fixation of two bodies in orthopedic surgery. Once the suture is around the two bodies, the ends of suture are formed into a traditional knot, or held by the knotless construct, to keep the suture around the two objects at a fixed length and able to support a load. Traditional knots depend on the tight, tortuous path created by pulling the limbs of the suture material to keep the suture loop from growing under load. However, once the knot is constructed, it is unable to be repositioned using the two ends of suture available. The construct is often in a location such that other bodies may contact the knot, which may cause the knot to loosen. Further, if other bodies contact the knot, the knot may irritate surrounding tissue.

Knotless constructs work to improve upon knots with the ability to be quick to construct and reducible in size. Knotless constructs of a reduced size limit the risk of any potentially irritating body while maintaining strength. Knotless constructs often depend on another clamping body separate from the suture, such as a "finger-trap" mechanism, or tension between the two objects to provide pressure on the suture, or a combination of these factors to keep the suture loop from growing under load. Clamping bodies add complexity to the construct and allow for additional points of failure. The "finger-trap" mechanism requires tension across the axis of the "finger-trap," which may slip if tension is not maintained across the axis. Changes in loading between the two objects may fluctuate, or significant tension between the two objects may be undesirable and make pressure on the suture ineffective to keep the suture from slipping. While low profile compared to traditional knots, knotless constructs often have areas of increased size which can cause irritation.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional knot or knotless suture constructs. For example, knots and knotless constructs can be large enough to cause irritation without a means for repositioning. Therefore, a need exists for a simple to use locking suture construct with a means for repositioning, tightening and loosening the construct without releasing tension therefrom. Various embodiments of the present invention may be advantageous in that they may solve or reduce one or more of the potential problems and/or disadvantages discussed herein.

The present disclosure is directed to an inventive configuration, structure, and resulting function of an adjustable locking suture construct comprised of suture material with a first end and a second end, each attached to a first body in a slidable manner, a constricting member formed in the second end of the suture material, and a bight in the suture material between the first end and the second end. A locking loop in the suture material is formed when the bight is passed through the constricting member around a second body.

When the locking suture construct is employed, a fixation loop secures a first body in relative position to a second body. The fixation loop comprises a fourth limb and a first limb. A positioning loop secures a constricting member in first position relative to the first body. The positioning loop comprises a second limb and a third limb. The fourth limb comprises the constricting member. The first limb and the second limb are threaded through the constricting member and form a locking loop.

According to an another aspect, a method of securing a first body in relative position to a second body includes (but is not limited to) the steps of: providing a locking suture construct having suture material with a first end and a second end, each attached to a first body in a slidable manner, a constricting member formed in the second end of the suture material, and a bight in the suture material between the first end and the second end; pulling the bight through the constricting member around a second body to create a locking loop; passing the first end and the second end of the suture material through the locking loop; pulling the locking loop while holding the first end of the suture material in a fixed position to increase a perimeter of the locking loop to a first predetermined size; pulling on the first end to decrease the perimeter of the locking loop to a second predetermined size smaller than the first predetermined size; and after the locking loop reaches the second predetermined size to move or rotate the constricting member past the second body toward the first body to a first position.

Suture material or sutures, as the terms are used and described herein, include monofilament or multi-filament suture as well as any other metallic or non-metallic filamentary or wire-like material suitable for performing the function of a suture. This material can include both bioabsorbable and non-absorbable materials.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which:

FIG. 3G is a magnified perspective view schematic representation of an adjustable constricting member construct according to an embodiment;

DETAILED DESCRIPTION OF THE INVENTION

Figure 1:
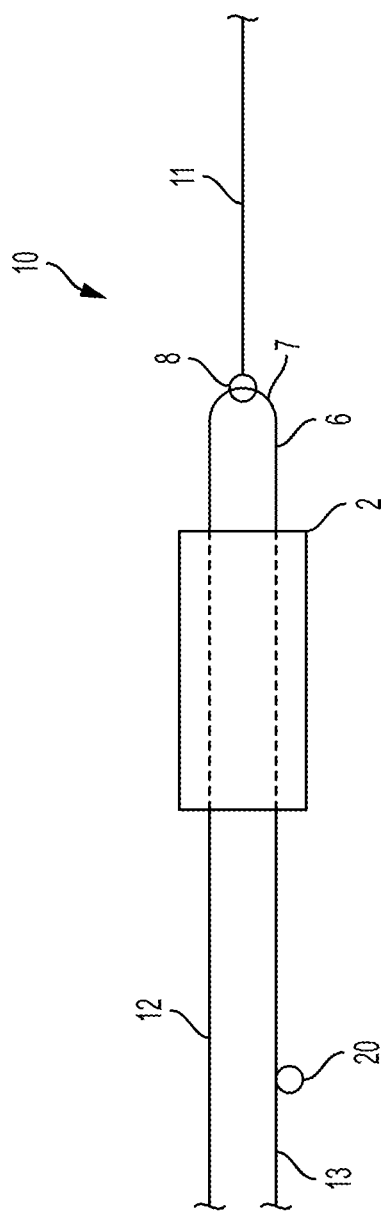
FIG. 1 is a perspective view schematic representation of a locking suture construct with an anchor according to an embodiment.

Referring now to the drawings, wherein like reference numerals refer to like parts throughout, there is seen in FIG. 1 an illustrative embodiment of the locking suture construct 10 with a slidably attached suture anchor 2. A purpose of the locking suture construct 10 in the illustrative embodiment discussed herein is to secure the suture anchor 2 in relative position to a tissue 18 via a fixation loop 30 with a fixed size and tension, as shown for example in FIG. 14 (described further below), where the suture anchor 2 can represent a first body (B) and the tissue 18 can represent a second body (A) (see, e.g., FIG. 15).

Figure 2:
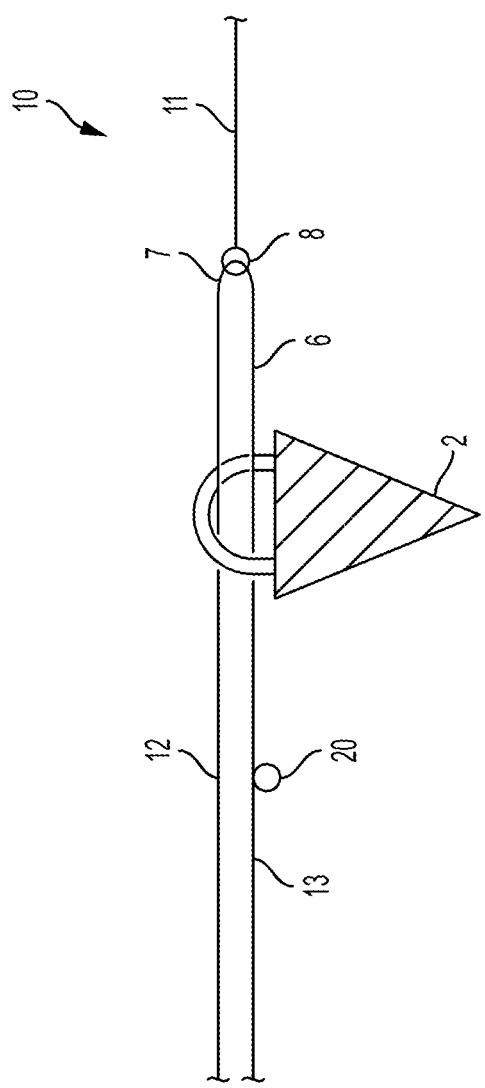
FIG. 2 is a perspective view schematic representation of a locking suture construct with an anchor according to an alternative embodiment.

In accordance with multiple embodiments, the first body (B) can be a suture anchor as shown in FIGS. 1 and 2, a surgical button (for use in, e.g., ACL repair), or a bone such as the coracoid process (for use in, e.g., bone to bone or bone to soft tissue fixation), as long as the locking suture construct 10 can be attached in an adjustable (e.g., slidable) manner to the first body (B). In the depicted embodiment of FIG. 1, for example, the suture anchor 2 can be an all-suture anchor, such as a Y-Knot® anchor (as should be understood and appreciated by those of ordinary skill in the art in conjunction with a review of this disclosure). In an alternative embodiment shown in FIG. 2, the suture anchor 2 can be a rigid suture anchor, such as the Revo® anchor or CrossFT® anchor (as should be understood and appreciated by those of ordinary skill in the art in conjunction with a review of this disclosure). Similarly, the second body (A) can be soft tissue as shown for example in FIG. 14, or a tendon, a bone block, or a bone such as a clavicle (as should be understood and appreciated by those of ordinary skill in the art in conjunction with a review of this disclosure). Notwithstanding these examples, the structure, configuration, use and functionality of the embodiments of the locking suture construct 10 described herein are not dependent on the particulars of the first body (B) and the second body (A). Stated differently, the first body (B) and the second body (A) can be any two objects, and the locking suture construct 10 can generally be structured, constructed and function in the same manner as described herein.

Referring back to FIG. 1, the locking suture construct 10 can include a length of suture material 6 having a first end or strand 12 and a second end or strand 13. As shown, the suture material 6 can be threaded through a loop 8 in a control line 11 and then through the suture anchor 2 (from right to left in FIG. 1) such that the first end 12 and the second end 13 of the suture material 6 are preferably relatively equal in length and parallel. Alternatively, any similar instrument (or no instrument at all, e.g., a user's finger), can be used in place of control line 11 and perform all of the functions of control line 11 as described herein and below (such as a gripper, a device with a hook, or any other grabbing or gripping device as should be understood by those of skill in the art in conjunction with a review of this disclosure) by grabbing or catching bight 7 formed in suture material 6 (see, e.g., bight 7 shown in FIGS. 1, 2, 4, 5, 6, 7, 8, 9, 10, 11, 17, 18, 19, 21).

The locking suture construct 10 can also include a constricting member, which can be fixed or adjustable. As described further below and illustrated in the Figures, each of the embodiments of the constricting member is formed as part of a structural intersection construct through which other portions of the suture 6 and a control line 11 or a threader 21 pass. Each constricting member embodiment is configured to move along/rotate around fixation loop 30 to an optimal position as determined by a user, i.e., medical professional (compare, for example, the positioning of the constricting member in FIG. 12 with FIG. 14, and the positioning of the constricting member in FIG. 13 with FIG. 15), while the fixation loop 30 preferably maintains a fixed size and tension about first body (B) and second body (A). The constricting member can be formed as an adjustable locking splice/constricting member 20 as shown in FIGS. 3A-3B, an alternative adjustable constricting member 20' as shown in FIGS. 3C-3D, a fixed constricting member 20'' as shown in FIG. 3E, another alternative adjustable constricting member 20''' as shown in FIGS. 3F-3G, or any other similar enclosed boundary component (as should be understood and appreciated by those of ordinary skill in the art in conjunction with a review of this disclosure).

Figure 3A:
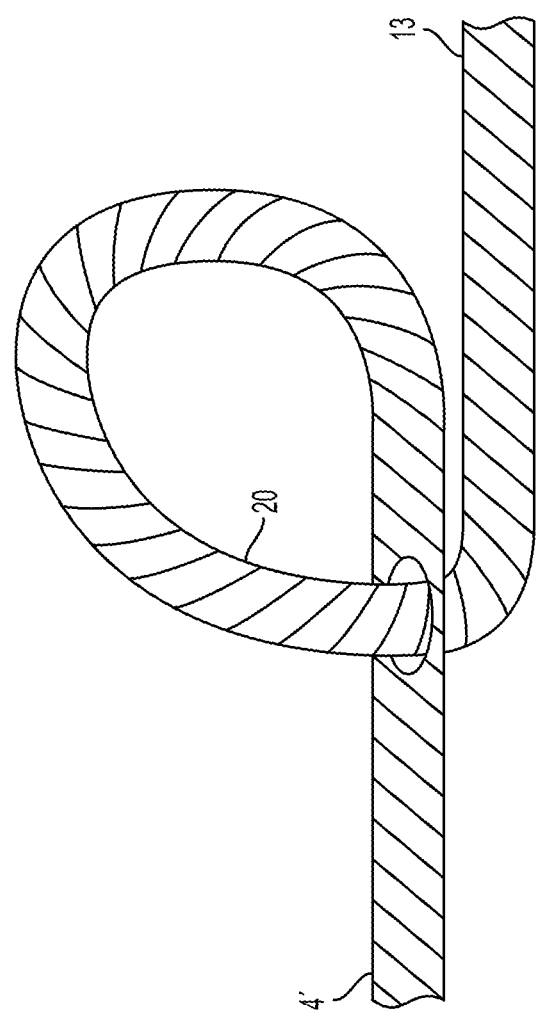
FIG. 3A is a magnified perspective view schematic representation of an adjustable constricting member constricting member construct according to an embodiment.
Figure 3B:
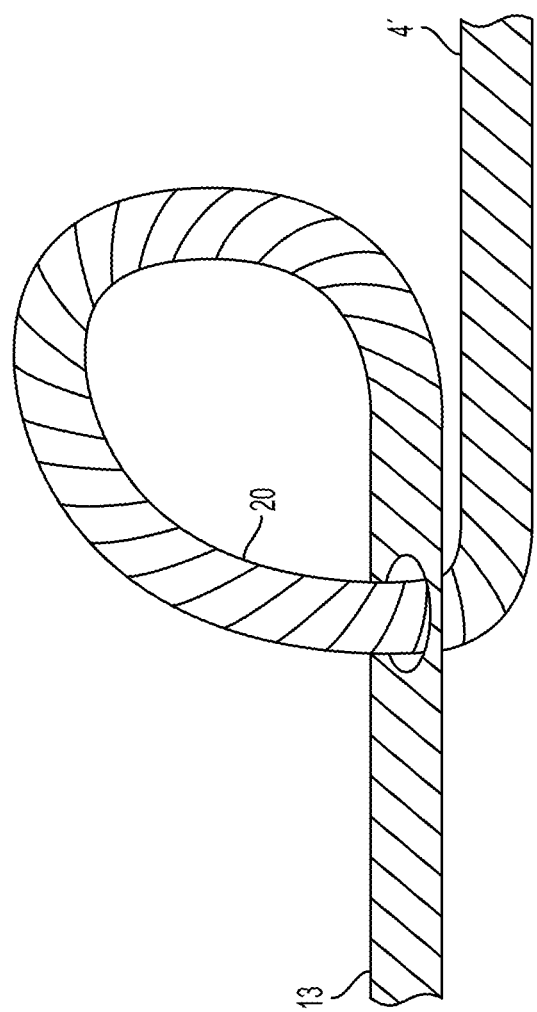
FIG. 3B is a magnified perspective view schematic representation of an adjustable constricting member constricting member construct according to an embodiment.

Turning to FIGS. 3A-3B, schematic representations of an adjustable constricting member 20 are shown. Adjustable constricting member 20 is formed of a loop created by the second end 13 of the suture material 6 (or portion 4) being passed through itself in one direction or the other. The embodiment shown in FIG. 3A is configured such that second end 13 moves to the right (is pulled) to shrink the size of the hole formed by adjustable constricting member 20. The embodiment shown in FIG. 3B is configured such that portion 4' moves to the right to shrink the size of the hole formed by adjustable constricting member 20. The adjustable constricting member 20 is the embodiment of the constricting member used in certain example figures illustrating the use and functionality of the constricting member, which is further detailed below.

Figure 3C:
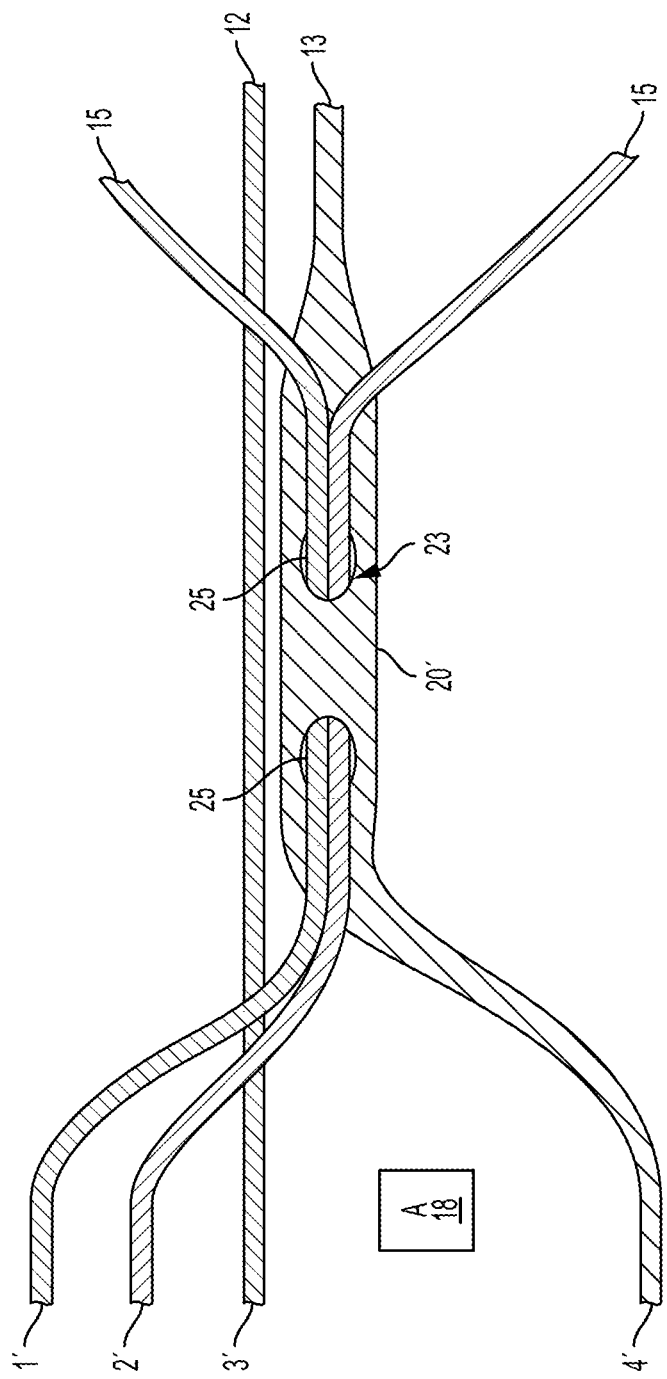
FIG. 3C is a magnified perspective view schematic representation of a locking splice constricting member construct of according to an embodiment.
Figure 3D:
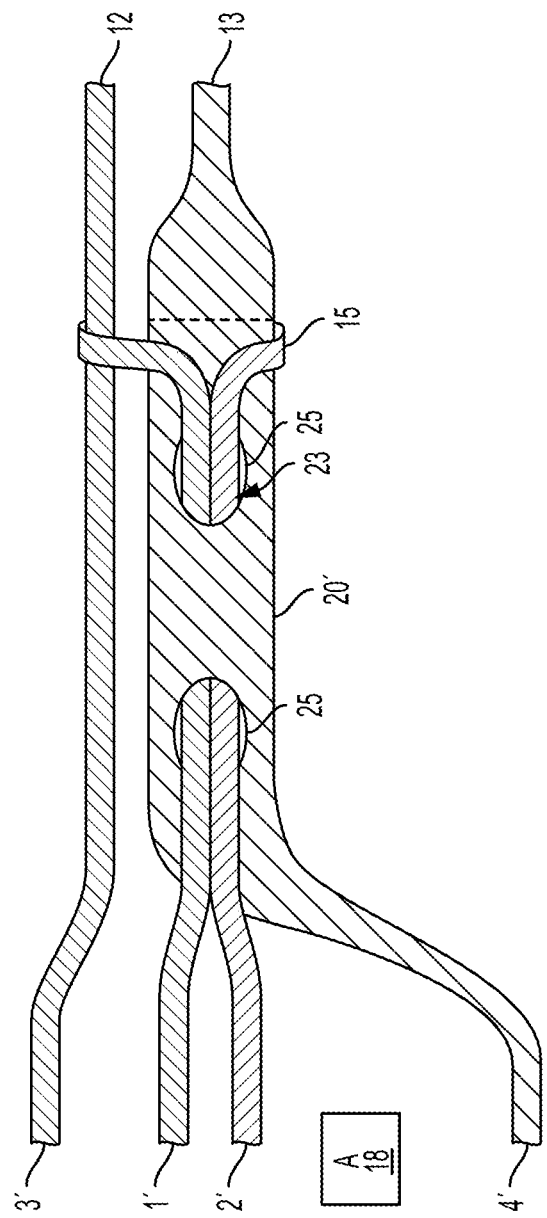
FIG. 3D is a magnified perspective view schematic representation of the locking splice constricting member construct of FIG. 3C with a reduced locking loop according to an embodiment.

Turning to FIGS. 3C-3D, schematic representations of a locking splice 20' are shown. Locking splice 20' is a fixed constricting member, and is formed of a segment of hollow round suture 23 between voids 25 in the wall of a length of hollow round suture.

Figure 3E:
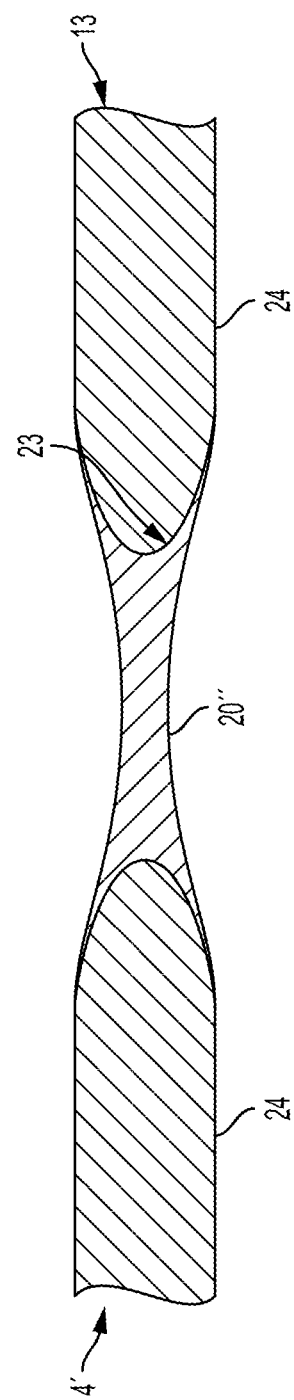
FIG. 3E is a magnified perspective view schematic representation of the fixed constricting member of FIG. 17 according to an embodiment.
Figure 3F:
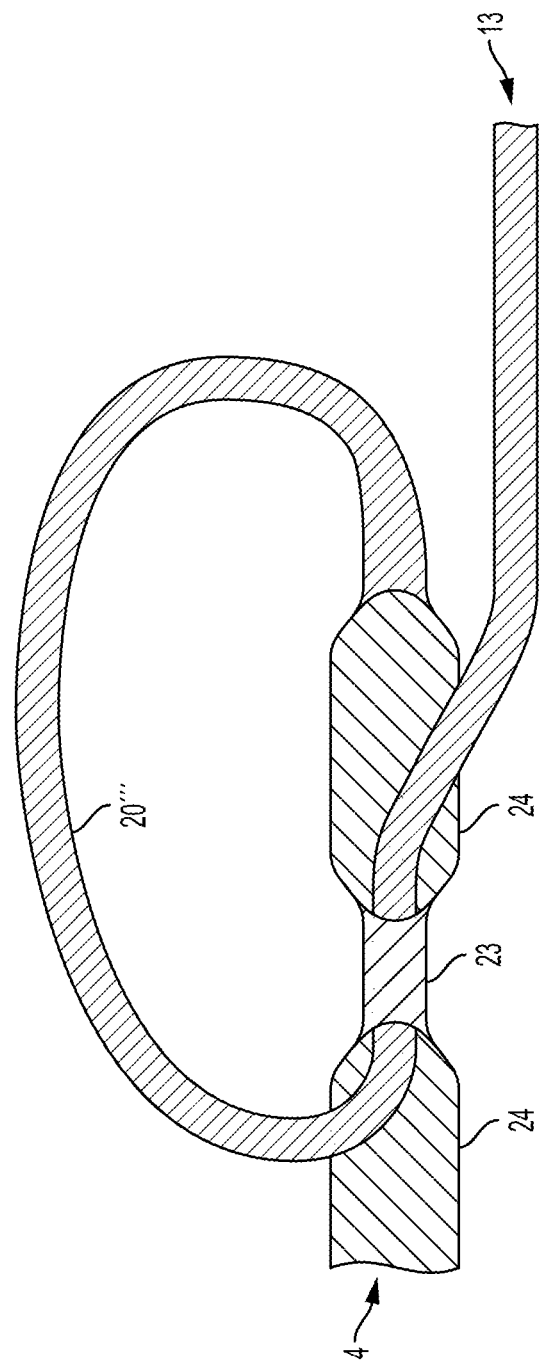
FIG. 3F is a magnified perspective view schematic representation of an adjustable constricting member construct according to an embodiment.

Turning to FIG. 3E, a schematic representation of another fixed constricting member 20'' is shown. The fixed constricting member 20'' is formed of a section of hollow round braided suture material 23 between sections of flat braided suture material 24.

Turning to FIGS. 3F-3G, schematic representations of another adjustable constricting member 20''' are shown. The adjustable constricting member 20''' is formed of a loop created by the second end 13 of suture material 6 being passed through a section of round suture material 23 between sections of flat suture material 24. As with the adjustable constricting member 20', the perimeter of the adjustable constricting member 20''' is reduced when the threaded piece of suture material, either the threaded limb 4 or second end 13, is pulled.

Figure 4:
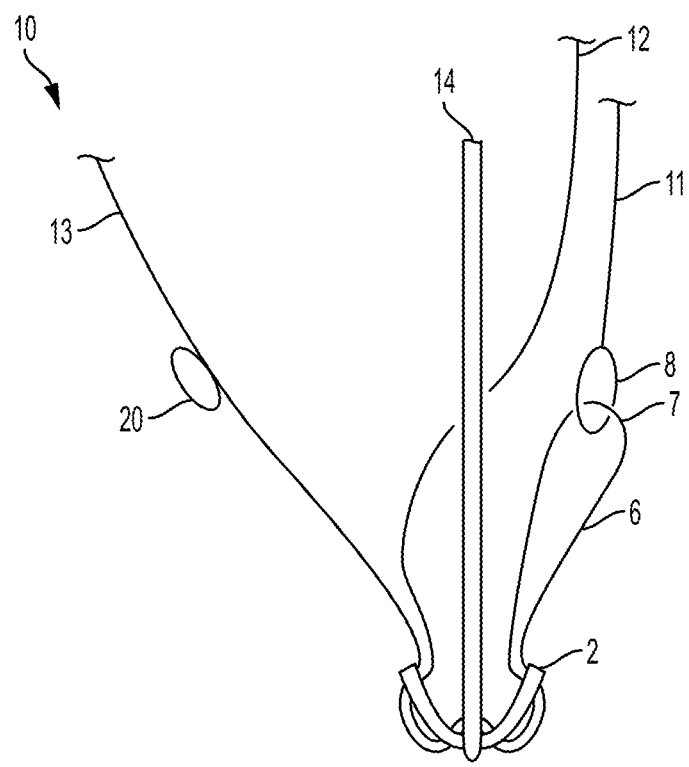
FIG. 4 is a side view schematic representation of the locking suture construct shown in FIG. 1 loaded onto an inserter according to an embodiment.

Referring now to FIG. 4, there is shown an illustrative embodiment of the locking suture construct 10 loaded on a suture anchor inserter 14. The suture anchor 2 is loaded onto the inserter 14, such as a Y-Knot® inserter (as should be understood and appreciated by those of ordinary skill in the art in conjunction with a review of this disclosure) such that the first end 12 is on a first side of the inserter 14 and the second end 13 is on a second side of the inserter 14. In the depicted embodiment, the inserter 14, suture anchor 2, and the locking suture construct 10 are shown in a pre-bone installation position and configuration, and both the control line 11 and the first end 12 are on the first side of the inserter 14. However, in this position and configuration, the control line 11 may alternatively be on the second side of the inserter 14 with the second end 13.

Figure 5:
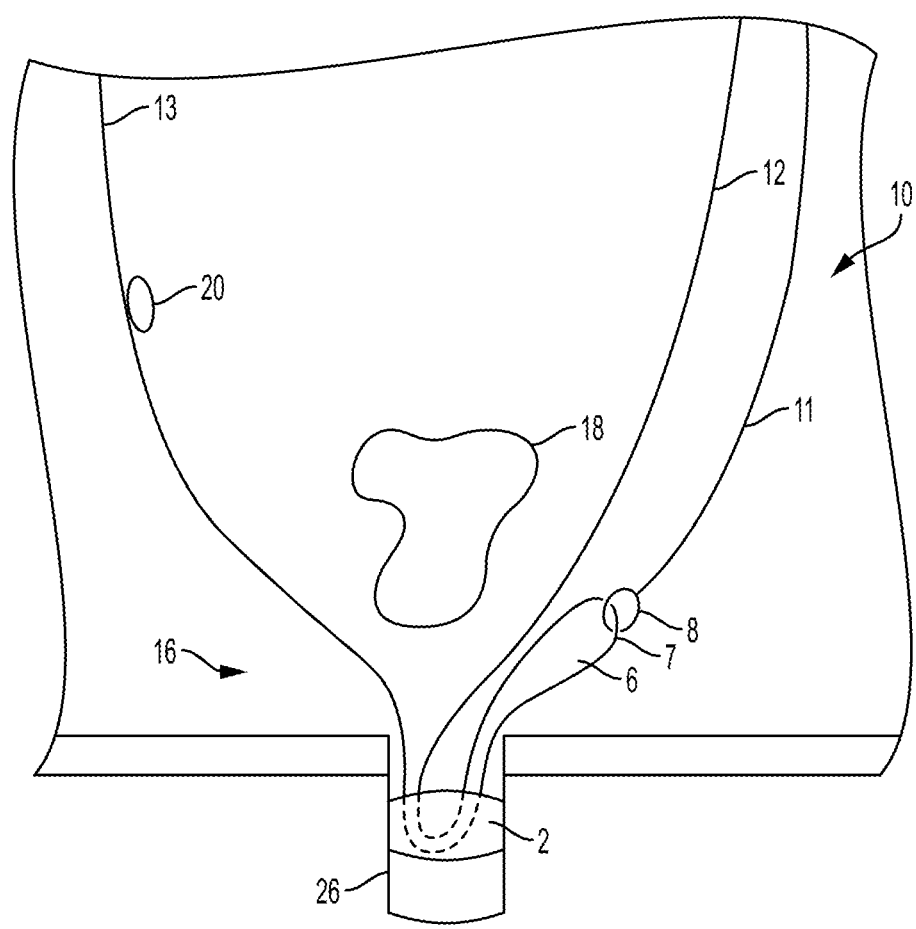
FIG. 5 is a side view schematic representation of the locking suture construct shown in FIG. 1 implanted in a bone hole via the anchor according to an embodiment.
Figure 6:
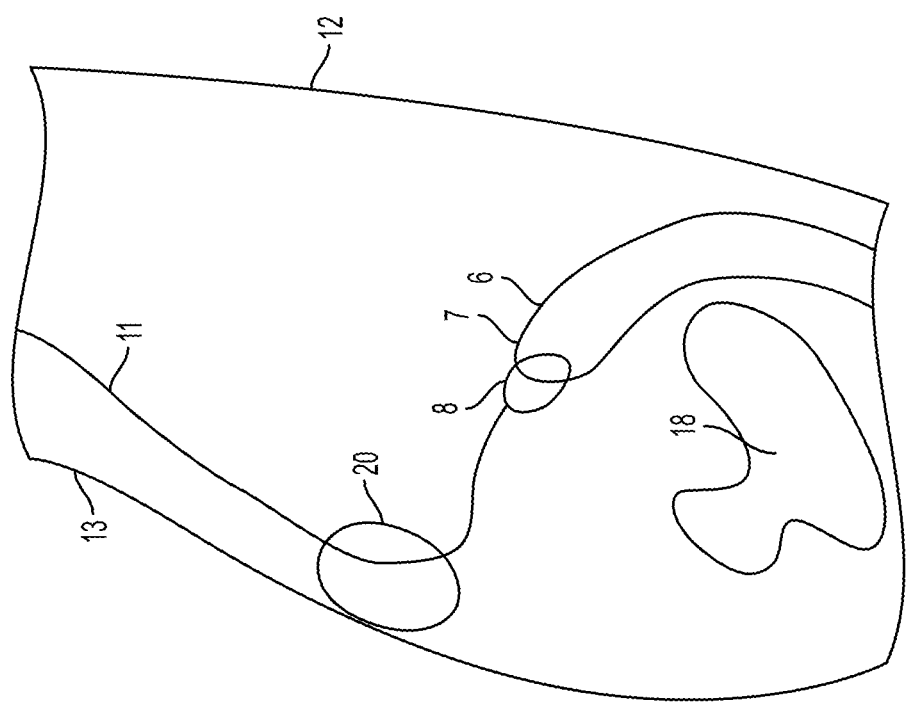
FIG. 6 is a perspective view schematic representation of a control line threaded through a constricting member around the tissue shown in FIG. 5 according to an embodiment.

Once the locking suture construct 10 is loaded onto the inserter 14, the inserter 14 can be used to implant the suture anchor 2 within a bone hole 26 formed in bone 16, as shown in FIG. 5. In the illustrative embodiment, the suture anchor 2 is placed within the bone hole 26 such that the first end 12 of suture material 6 and the control line 11 are on a first side of a tissue 18. As similarly stated above, the control line 11 may alternatively be on the second side of the tissue 18 with the second end 13 of the suture material 6.

Figure 7:
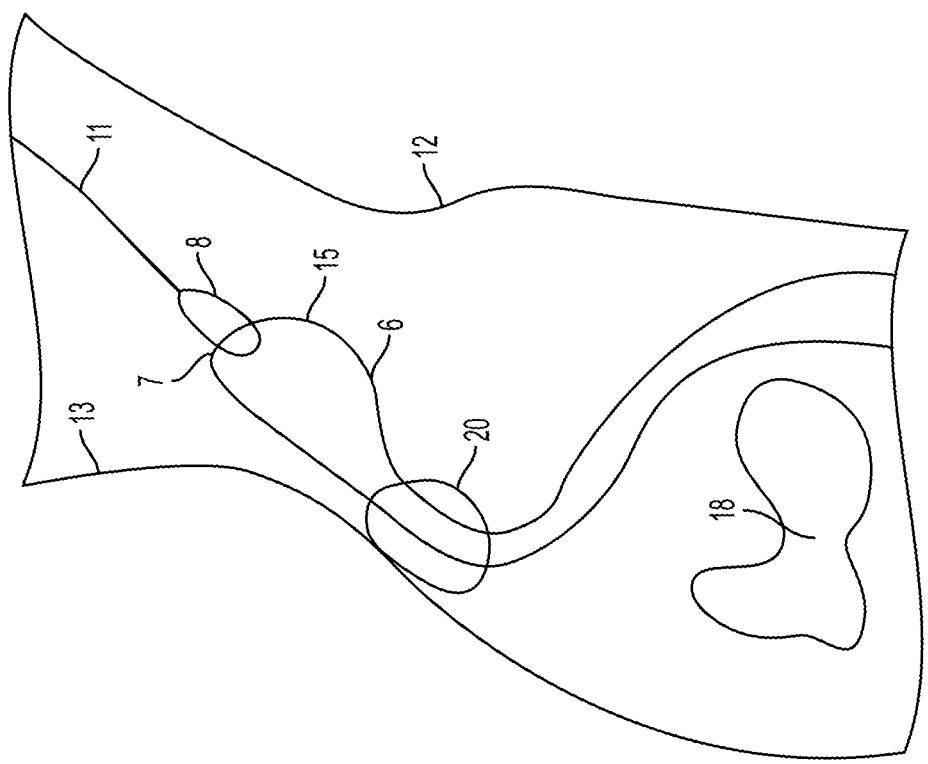
FIG. 7 is a perspective view schematic representation of a locking loop formed in the suture material according to an embodiment.

FIGS. 6-16 depict the steps to alter and fix the relative distance between the suture anchor 2 and the tissue 18 using the locking suture construct 10. First, in FIG. 6, the control line 11 is threaded through the constricting member 20. As shown in the depicted embodiment, the control line 11 is fed through the constricting member 20 formed on the second end 13 positioned above the tissue 18. Then, as shown in FIG. 7, the control line 11 and loop 8 and a portion of suture material 6 are fully pulled through the constricting member 20, creating a locking loop 15 with portion of the suture material 6 that was pulled through constricting member 20. As the perimeter of locking loop 15 grows per the continued pulling of the control line 11, the constricting member 20 is configured to move toward the tissue 18.

Figure 8:
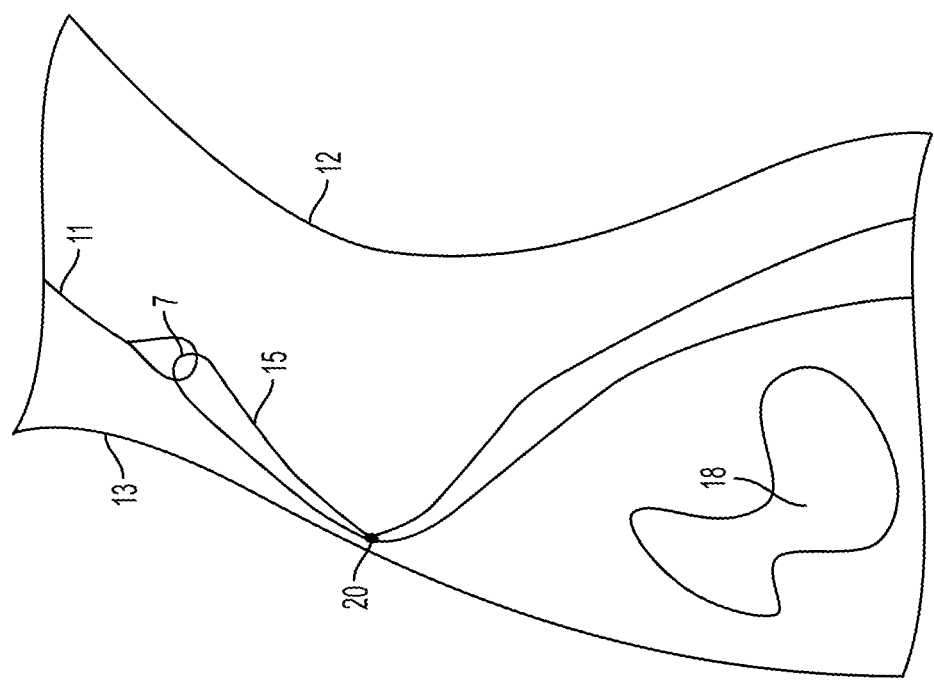
FIG. 8 is a perspective view schematic representation of the locking suture construct of FIG. 7 with a reduced constricting member according to an embodiment.
Figure 9:
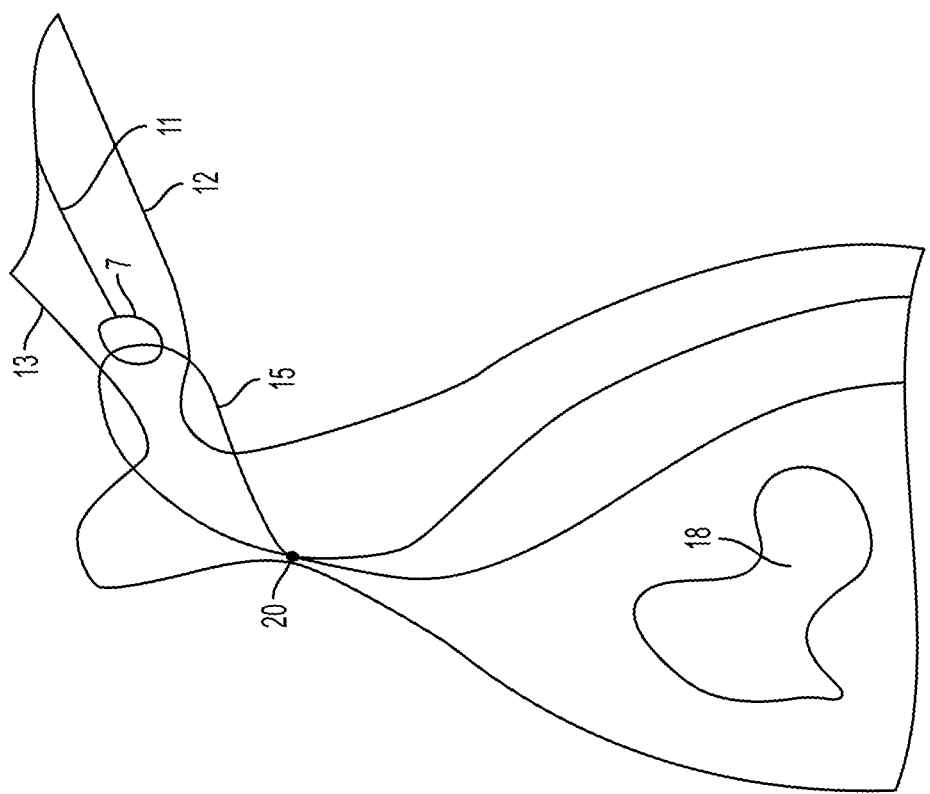
FIG. 9 is a perspective view schematic representation of a first end and a second end of suture material threaded through the locking loop of FIG. 7 according to an embodiment.
Figure 10:
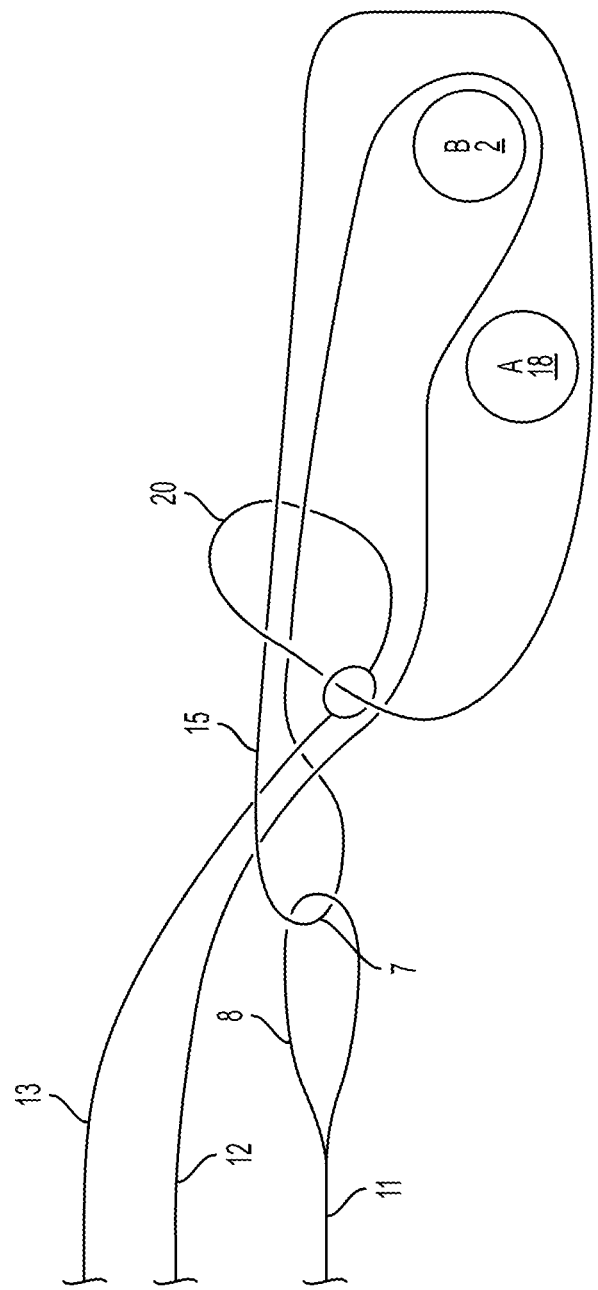
FIG. 10 is an extended perspective view schematic representation of the locking suture construct similar to FIG. 9 according to an embodiment.

Although shown expanded for clarity, the constricting member 20 in FIG. 7 is preferably actually tight around the locking loop 15, as shown in FIG. 8, pursuant to pulling on second end 13 (in the upward direction as shown in FIG. 8). Next, referring now to FIG. 9, the first end 12 and the second end 13 of the suture material 6 are passed through the locking loop 15. FIG. 10 depicts the first end 12 and the second end 13 pulled through the locking loop 15, where the constricting member 20 is shown in an expanded configuration for clarity of the positioning of each of the reference components.

Figure 11:
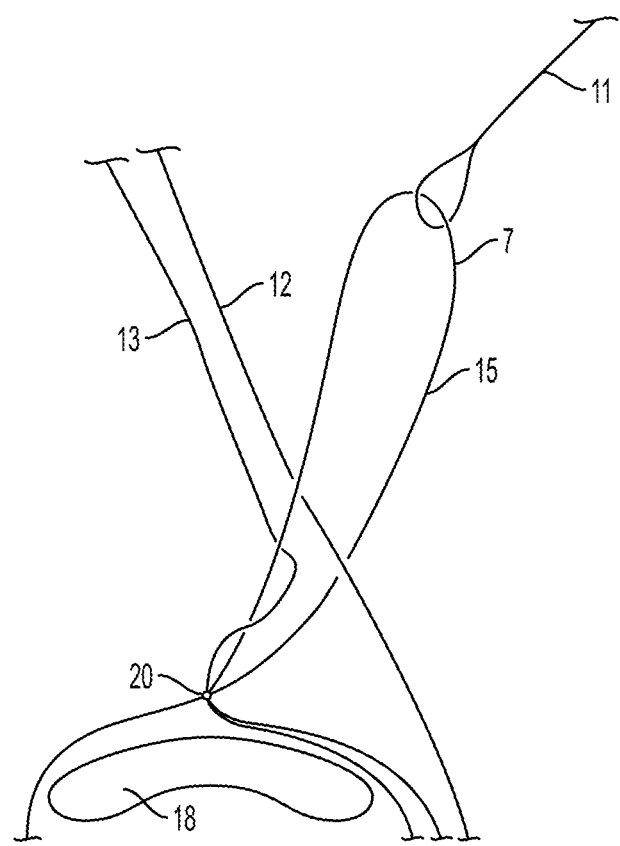
FIG. 11 is a perspective view schematic representation of a reduced constricting member in close proximity to the tissue according to an embodiment.
Figure 12:
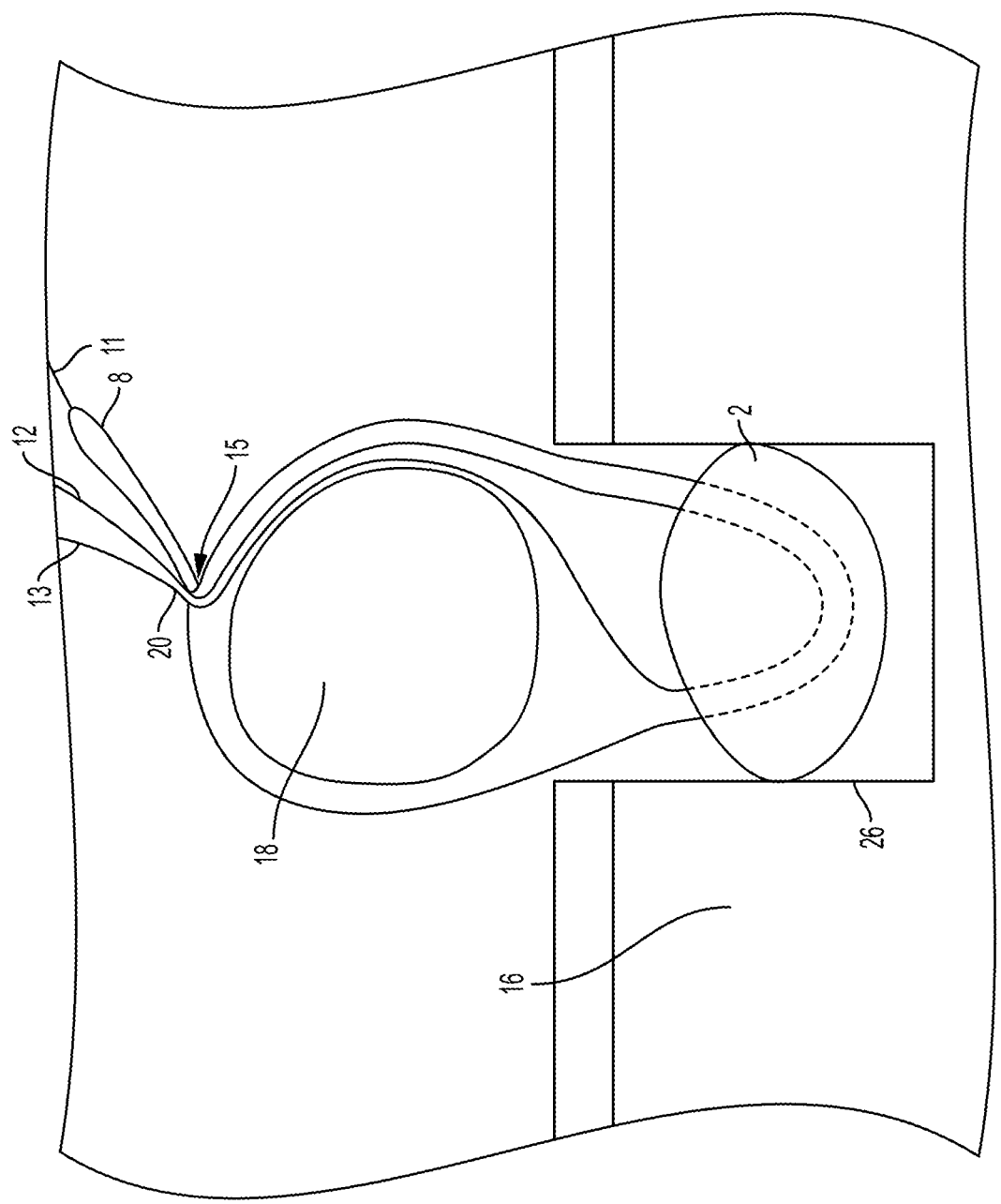
FIG. 12 is an extended perspective view schematic representation of the locking suture construct of FIG. 11 with a reduced locking loop according to an embodiment.
Figure 13:
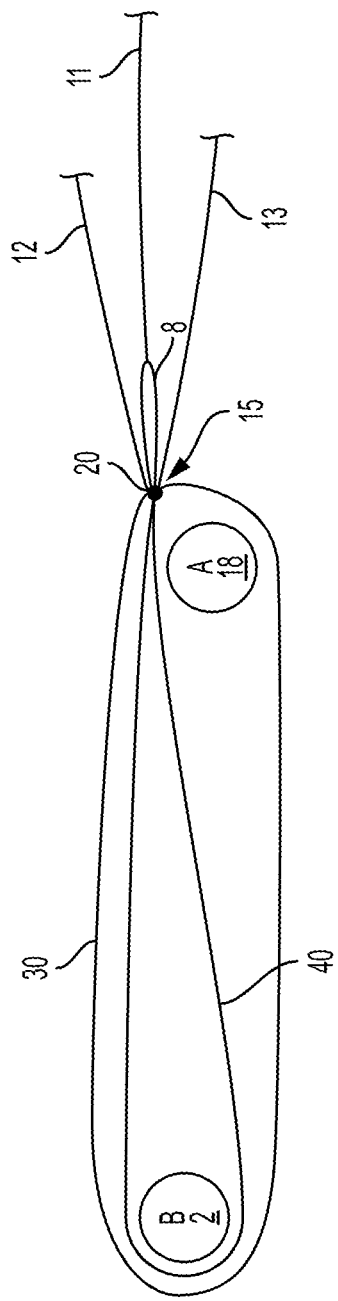
FIG. 13 is a top perspective view schematic representation of the locking suture construct of FIG. 12 according to an embodiment.

Referring now to FIG. 11, the first end 12 and the second end 13 are shown passed through the locking loop 15, which had previously been enlarged, moving the constricting member 20 against the tissue 18 as described above. With the constricting member 20 in close proximity to the tissue 18, the first end 12 is pulled to reduce the perimeter of the locking loop 15 to a minimum perimeter, as shown in the views of FIGS. 12 and 13. When the locking loop 15 is reduced, the locking loop 15 squeezes, pinches or "strangles" the first end 12 and the second end 13 to obtain a minimum working perimeter (where, for example, the inner surface of the locking loop 15 preferably fully contacts and applies pressure to the first end 12 and the second end 13; and/or where the inner surface of the locking loop 15 squeezes down to a point where if 1' and 2' are pulled separately/individually, they do not freely or easily move/slide through constricting member 20—see, e.g., FIG. 3D—as should be understood by a person of ordinary skill in the art in conjunction with a review of this disclosure). Tension is preferably maintained on the control line 11 while reducing the locking loop 15 (per the pulling of first end 12) until the locking loop 15 has a minimum working perimeter. Once locking loop 15 reaches the minimum working perimeter, fixation loop 30 is configured to maintain its size and tension about first body (B) and second body (A).

Figure 14:
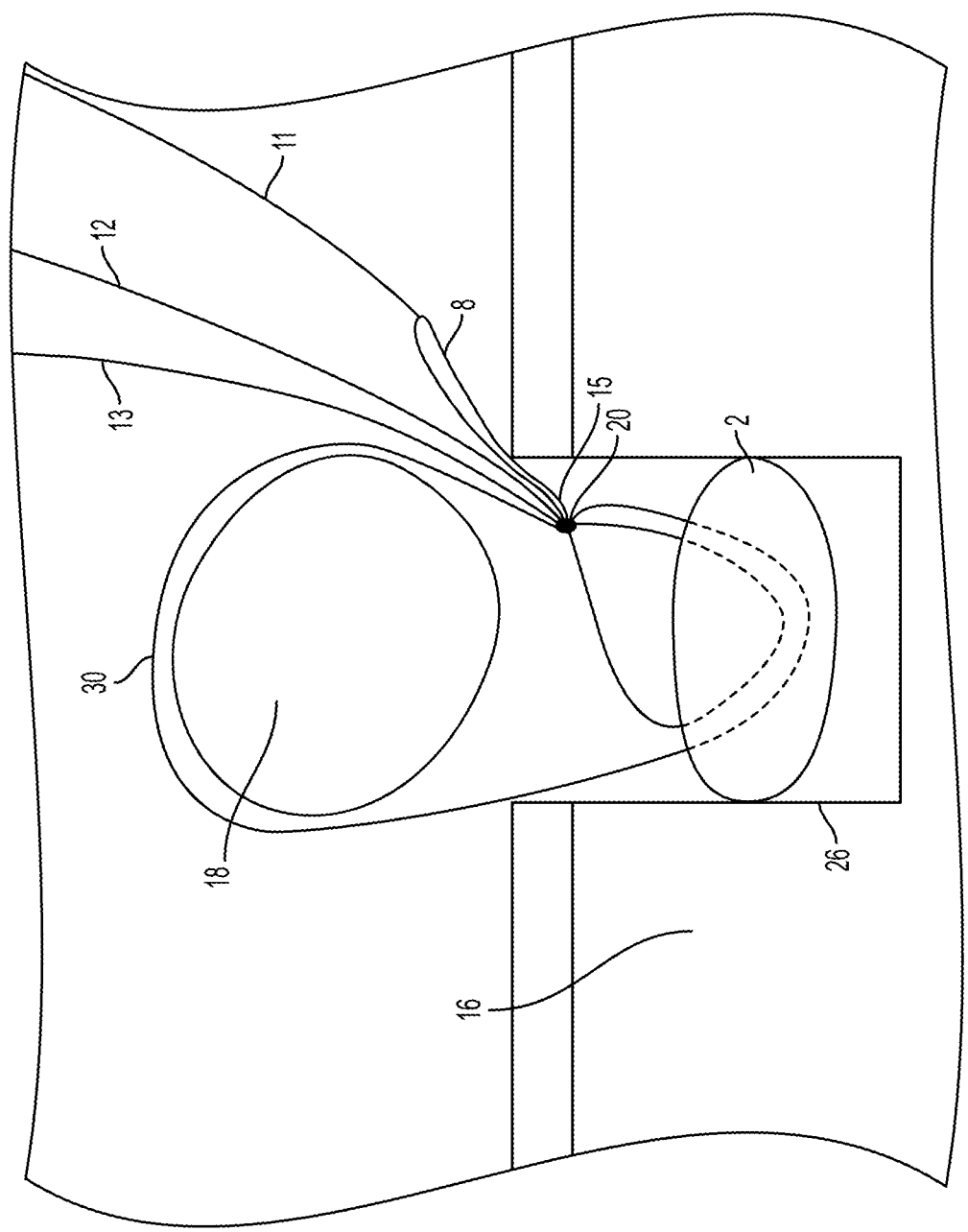
FIG. 14 is a perspective view schematic representation of the constricting member and locking loop rotated toward the anchor according to an embodiment.
Figure 15:
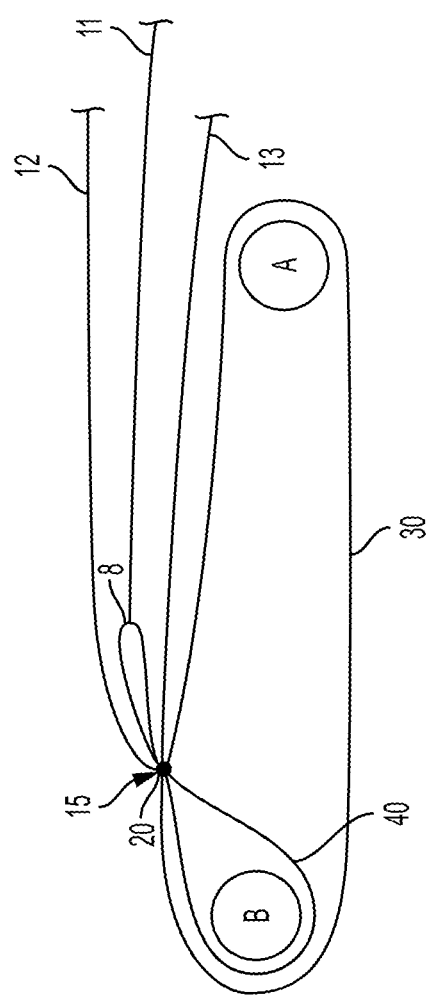
FIG. 15 is a top perspective view schematic representation of the locking suture construct of FIG. 14 according to an embodiment.
Figure 16:
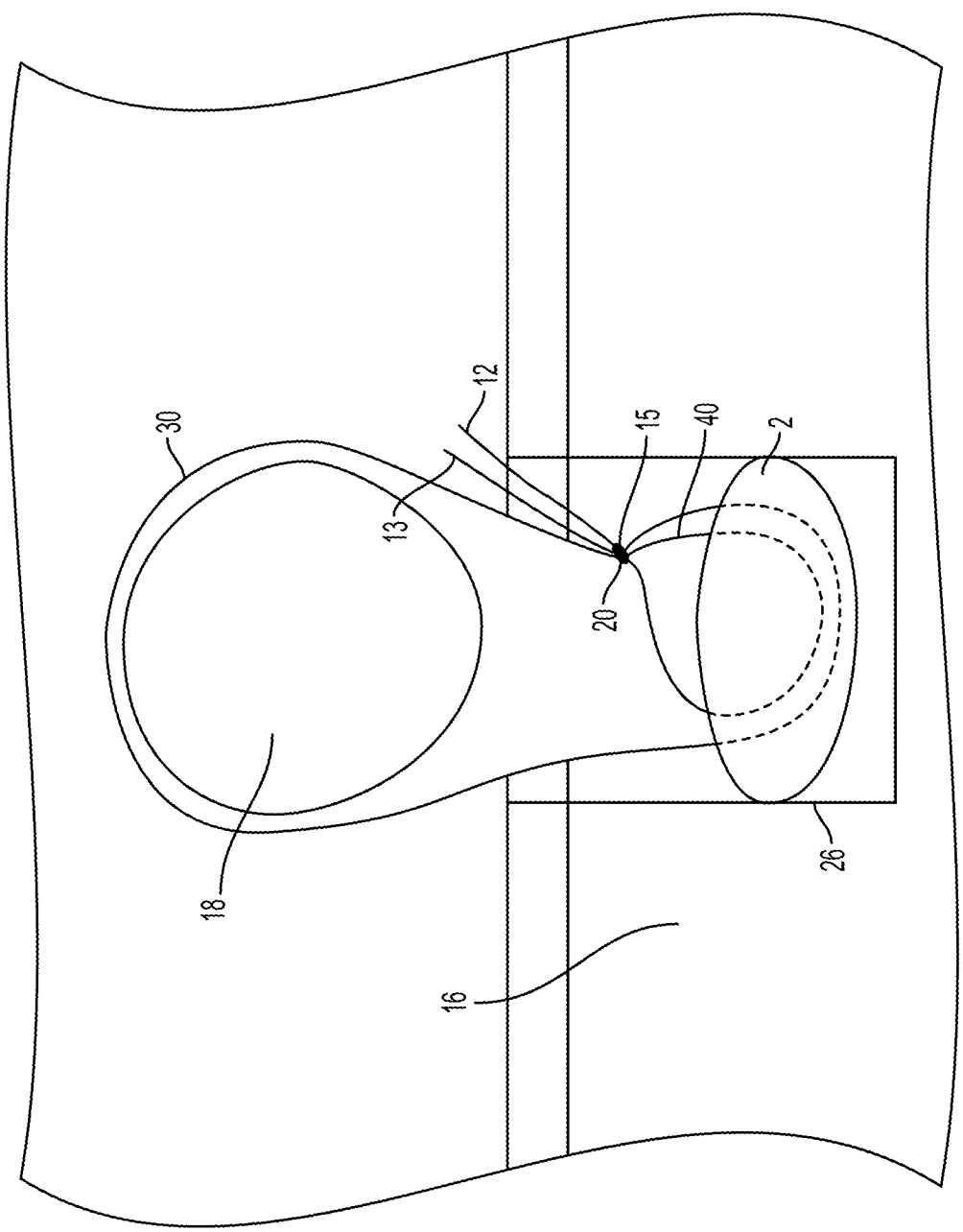
FIG. 16 is a perspective view schematic representation of the locking suture construct of FIG. 14 with an excess portion of the first end and the second end excised according to an embodiment.
Figure 17:
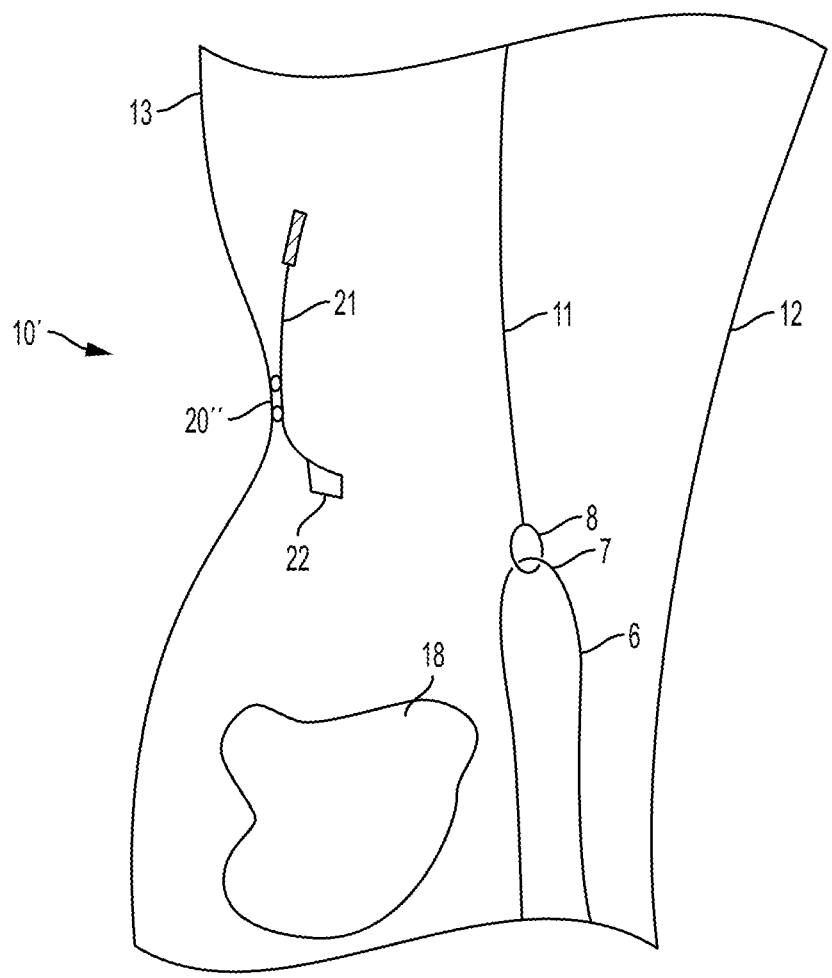
FIG. 17 is a perspective view schematic representation of a locking suture construct with a threader through a fixed constricting member according to an alternative embodiment.

With reference to FIGS. 14-15, if the first end 12 is continuously pulled after the locking loop 15 has reached a minimum perimeter, the constricting member 20 is configured to and begins to move/rotate toward the suture anchor 2 (while fixation loop 30 preferably still is configured to maintain its size and tension). As shown in FIGS. 14-15, as compared to FIGS. 12 and 13, respectively, the first end 12 can be pulled such that the constricting member 20 moves/rotates around the tissue 18 (from the position shown in FIGS. 12 and 13) until it is in close proximity to the suture anchor 2 or other optimal location as may be decided by the user. While first end 12 is pulled, positioning loop 40 becomes smaller (compare FIG. 13 with FIG. 15). Constricting member 20 can be a relatively bulky construct, and a user may prefer to move constricting member 20 towards first body (B) (within a bone hole 26) in a less irritating position to the patient. Finally, excess suture material 6 from the first end 12 and the second end 13 can be excised near the bone 16 to produce the end result of the locking suture construct 10 surrounding the tissue 18 (second body (A)) and the suture anchor 2 (first body (B)) in a post-bone installation position and configuration as shown in FIG. 16. Thus, the tissue 18 is held in a position relative to the suture anchor 2 by the locking suture construct 10. The relative position is ultimately secured with two loops, the fixation loop 30 and the positioning loop 40. The fixation loop 30 holds the tissue 18 (second body (A)) in relative position to the suture anchor 2 (first body (B)), while the positioning loop 40 holds the constricting member 20 in a desirable position such that irritation and trauma is reduced.

However, if the constricting member 20 moves or is rotated to an undesirable or non-optimal position with respect to the tissue 18 and the suture anchor 2, the locking suture construct 10 can be repositioned as long as the first end 12 and second end 13 have not been cut. To reposition the locking suture construct 10, the control line 11 is pulled and the constricting member 20 moves/rotates away from the suture anchor 2 and back toward the tissue 18. As the constricting member 20 moves/rotates, the perimeter of the locking loop 15 grows (essentially performing the above referenced steps in reverse order). This allows the locking suture construct 10 to be repositioned in a desirable area, for example, an area where the constricting member 20 will cause less irritation or trauma to the surrounding tissue or bone. In accordance with an alternative embodiment, second end 13 can be pulled instead of control line 11 to obtain the same results as discussed in this paragraph.

In an alternative embodiment shown in FIGS. 17-20, the illustrated constricting member of the locking suture construct 10' is not adjustable and is instead a fixed constricting member (e.g., fixed constricting member 20" shown in FIG. 3E) to be used in conjunction with a threader 21.

Figure 18:
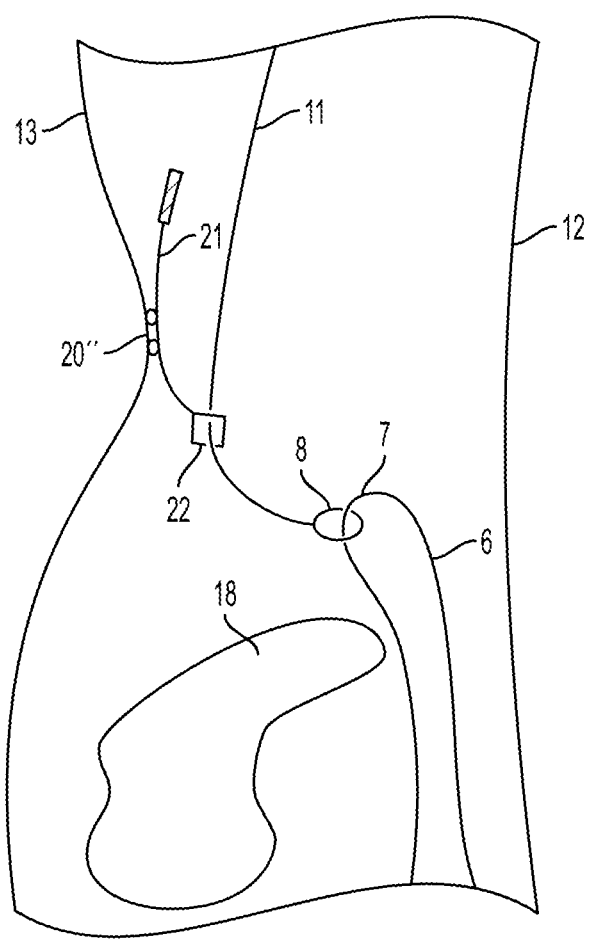
FIG. 18 is a perspective view schematic representation of a control line pulled through the eyelet of the threader according to an alternative embodiment.
Figure 19:
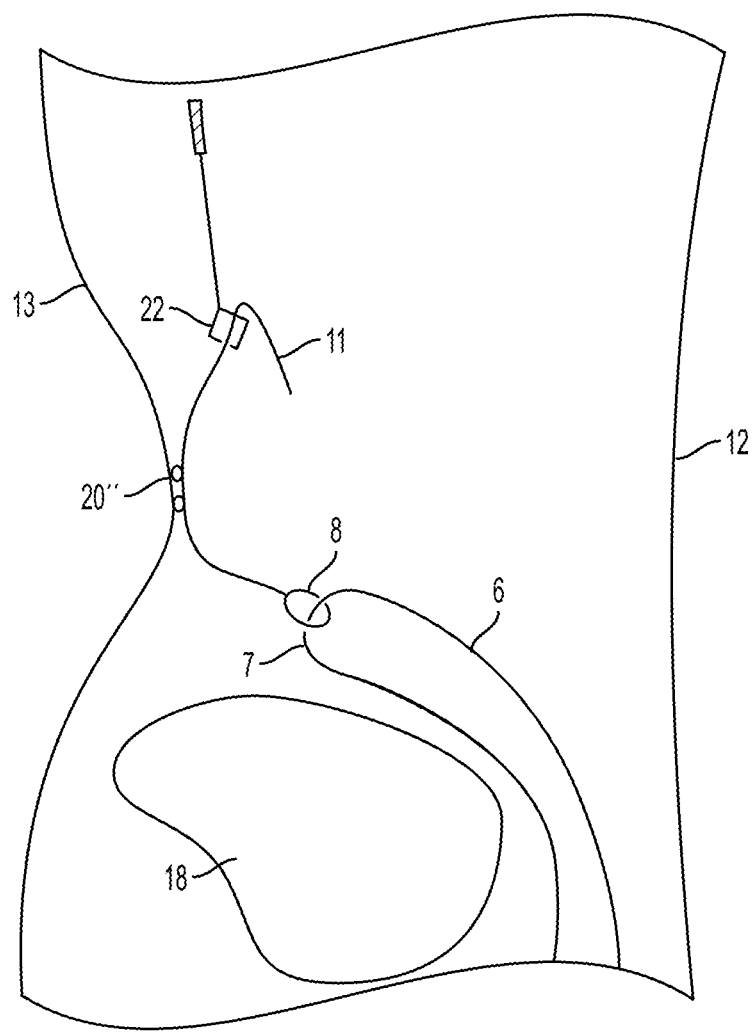
FIG. 19 is a perspective view schematic representation of the threader pulling the control line through the fixed constricting member according to an alternative embodiment.
Figure 20:
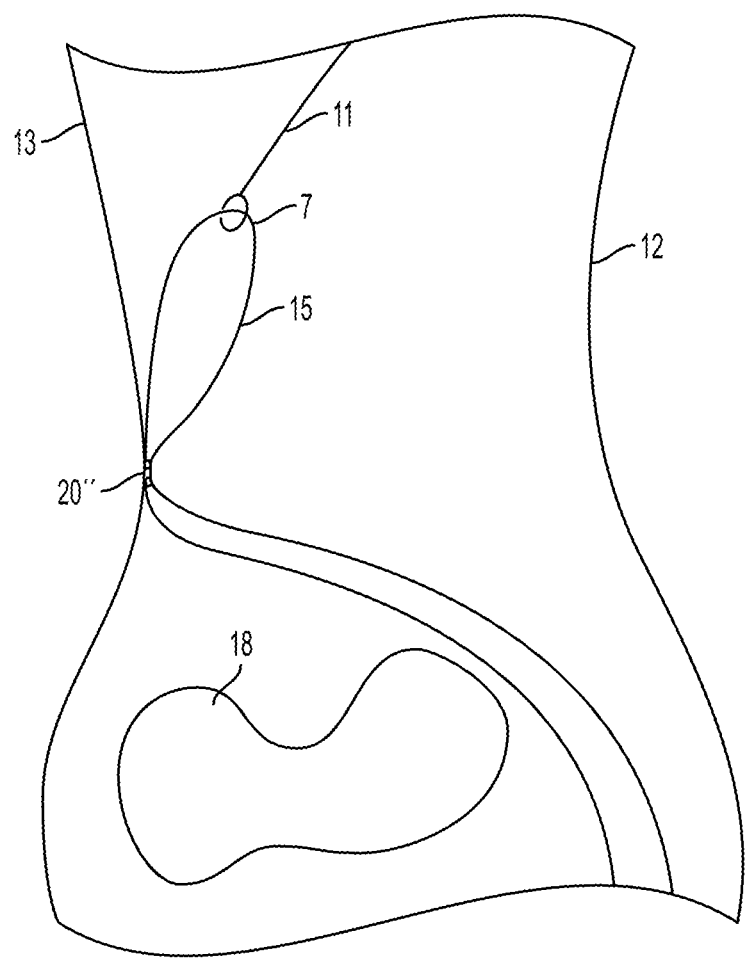
FIG. 20 is a perspective view schematic representation of a locking loop created by pulling the control line through the fixed constricting member according to an alternative embodiment.

Referring next to FIG. 18, the threader 21 is shown inserted through the hollow section 23 of the fixed constricting member 20". The eyelet 22 of the threader 21 extends through the fixed constricting member 20. As shown in the depicted embodiment, the control line 11 is being pulled through the eyelet 22 of the threader 21. Thereafter, with reference to FIG. 19, the threader 21 is pulled away from the fixed constricting member 20, such that the eyelet 22 holding the control line 11 is fully pulled through the fixed constricting member 20. Just as shown in and described with respect to FIG. 8, FIG. 20 depicts the control line 11 pulled through the constricting member 20 to create the locking loop 15. The steps shown and described with respect to FIGS. 8-16 apply equally to the fixed constricting member 20" alternative embodiment.

Figure 21:
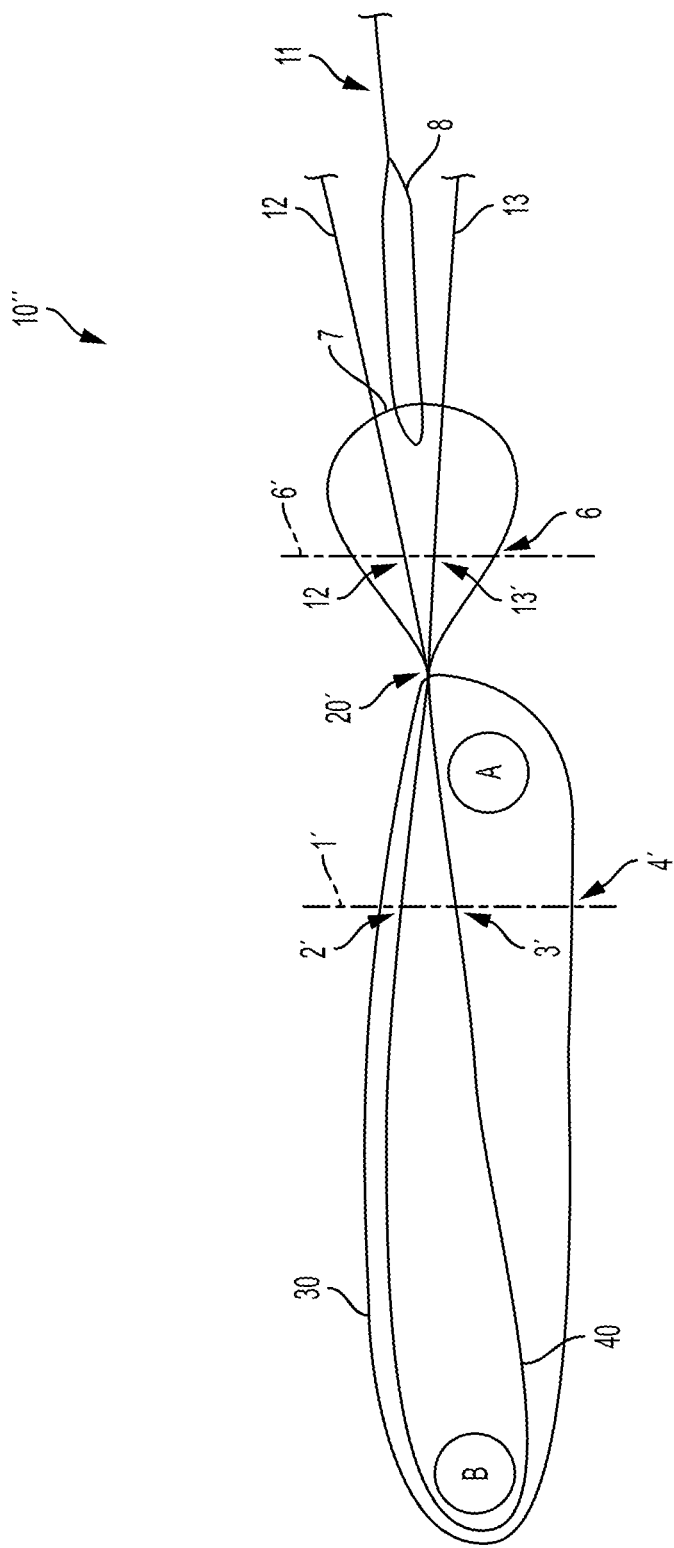
FIG. 21 is a top perspective view schematic representation of the locking suture construct with a locking splice construct as the constricting member according to an alternative embodiment.

Referring back to FIGS. 3C-3D, an alternative embodiment regarding the locking splice 20' constricting member construct is shown. FIG. 21 shows a top perspective view schematic representation of the locking suture construct 10"' using the locking splice 20' according to this alternative embodiment. In the depicted embodiment, the second body (A) is in a first position relative to the first body (B). As shown, both the first end 12 and the second end 13 have been pulled through the locking loop 15.

Referring back to FIG. 3C, there is shown a magnified view of the locking splice construct 20'. In the depicted embodiment, the locking splice construct 20' is formed in a fourth limb 4', which is in the second end 13 of the suture material 6, similar to that shown in FIG. 1 and also shown in FIG. 21. The locking loop 15 has a first limb 1' and a second limb 2', which extend through the locking splice construct 20'. In addition, the first end 12 of the suture material 6 which has been passed through the locking loop 15, extends through the locking splice construct 20' as a third limb 3' on the same side of the second body (A) as the first limb 1' and the second limb 2'. The fourth limb 4' is the only portion of suture material 6 shown on the opposing side of the second body (A). Ultimately, when the perimeter of the locking loop 15 is reduced to the minimum working perimeter, the first limb 1' and the second limb 2' are pulled through the locking splice construct 20 until the locking loop 15 is tightly wrapped around the third limb 3' and the fourth limb 4', as shown in FIG. 3D. The steps shown and described with respect to FIGS. 8-16 apply equally to the locking splice 20' alternative embodiment.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A locking suture construct, comprising:
   a fixation loop securing a first body in relative position to a second body;
   wherein the fixation loop comprises a fourth limb having a constricting member and a first limb;

a positioning loop securing the constricting member in a first position relative to the first body;

wherein the positioning loop comprises a second limb and a third limb;

the first limb and the second limb are threaded through the constricting member and form a locking loop; and wherein the size of the positioning loop is configured to be reduced and the constricting member is configured to move towards the first body by pulling the third limb in a direction away from the positioning loop and the constricting member.

2. The locking suture construct of claim 1, further comprising a control line secured around the locking loop.

3. The locking suture construct of claim 2, wherein the size of the positioning loop is configured to be increased and the constricting member is configured to move towards the second body by pulling the control line or a second end of a suture material attached to the first body in a direction away from the positioning loop and the constricting member.

4. The locking suture construct of claim 1, wherein the constricting member is selected from the group consisting of an adjustable constricting member and a fixed constricting member.

5. A locking suture construct, comprising:
a fixation loop securing a first body in relative position to a second body;
wherein the fixation loop comprises a fourth limb having a constricting member and a first limb;
a positioning loop securing a constricting member in a first position relative to the first body;
wherein the positioning loop comprises a second limb and a third limb;
the first limb and the second limb are threaded through the constricting member and form a locking loop;
a control line secured around the locking loop; and
wherein the size of the positioning loop is configured to be increased and the constricting member is configured to move towards the second body by pulling the control line or a second end of a suture material attached to the first body in a direction away from the positioning loop and the constricting member.

6. The locking suture construct of claim 5, wherein the size of the positioning loop is configured to be reduced and the constricting member is configured to move towards the first body by pulling the third limb in a direction away from the positioning loop and the constricting member.

7. The locking suture construct of claim 5, wherein the constricting member is selected from the group consisting of an adjustable constricting member and a fixed constricting member.

* * * * *